(12) United States Patent
Haberer et al.

(10) Patent No.: US 6,683,318 B1
(45) Date of Patent: Jan. 27, 2004

(54) ION BEAM THERAPY SYSTEM AND A METHOD FOR OPERATING THE SYSTEM

(75) Inventors: Thomas Haberer, Darmstadt (DE); Michael Kraemer, Darmstadt (DE); Gerhard Kraft, Darmstadt (DE); Wilma Kraft-Weyrather, Darmstadt (DE); Dieter Schardt, Darmstadt (DE); Michael Scholz, Darmstadt (DE); Ulrich Weber, Darmstadt (DE); Aleksiy Dolinski, Darmstadt (DE); Hartmut Eickhoff, Darmstadt (DE); Bernhard Franczak, Darmstadt (DE); Udo Krause, Darmstadt (DE); Juergen Klabunde, Darmstadt (DE); Ludwig Dahl, Darmstadt (DE); Marius Pavlovic, Darmstadt (DE); Ulrich Ratzinger, Darmstadt (DE); Bernhard Schlitt, Darmstadt (DE); Joerg Pawelke, Grosserkmannsdorf (DE); Rainer Hinz, Dresden (DE); Wolfgang Enghardt, Radeberg (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 0 days.

(21) Appl. No.: 09/786,698
(22) PCT Filed: Sep. 10, 1999
(86) PCT No.: PCT/EP99/06714
§ 371 (c)(1), (2), (4) Date: Jul. 10, 2001
(87) PCT Pub. No.: WO99/16342
PCT Pub. Date: Mar. 23, 2000

(30) Foreign Application Priority Data

Sep. 11, 1998 (EP) .................................... 98117256

(51) Int. Cl.$^7$ ................................................ A61N 5/01
(52) U.S. Cl. ........................................... 250/492.3
(58) Field of Search .................... 250/492.1, 492.3; 378/65; A61N 5/01

(56) References Cited

U.S. PATENT DOCUMENTS 4,870,287 A * 9/1989 Cole et al. ............... 250/492.3

OTHER PUBLICATIONS

Marius Pavlovic, "Beam–optics study of the gantry beam delivery system for light–ion cancer therapy", 1997, Nuclear Instruments and Methods in Physics Research, Elsevier, pp. 439–454.*

* cited by examiner

Primary Examiner—Judy Nguyen
Assistant Examiner—Blaise Mouttet
(74) Attorney, Agent, or Firm—Frommer Lawrence & Haug LLP; Ronald R. Santucci

(57) ABSTRACT

An ion beam therapy system and method for operating the system includes a source of ions (300), an accelerator system (400) and an ion beam transport system (60) for directing an ion beam to a plurality of treatment stations (100) to treat patients. The ion beam transport system (60) includes a gantry (8) carrying a vertical deflection system (45) and horizontal deflection system (55) positioned upstream from a last bending magnet (65) so as to provide a parallel scanning mode by an edge focusing effect.

30 Claims, 9 Drawing Sheets 3D view of the rotating gantry

Fig. 16

Section A-A

A Synchrotron
B Power Supplies
C Horizontal Beam
D Radioactive Waist
E Rotating Gantry
F Ventilation Fig. 2  Accelerator System

Fig. 3

Fig. 4    Synchrotron Ring

Fig. 5  *high energy beam transport system.*

Fig. 6

3D view of the rotating gantry

ION BEAM THERAPY SYSTEM AND A METHOD FOR OPERATING THE SYSTEM

The present invention relates to an ion beam therapy system used in the treatment of cancer and to a method for operating said system according to the preamble independent claims.

Such a therapy system is known for a proton beam from U.S. Pat. No. 4,870,287. The known system is selectively generating and transporting proton beams from a single proton source through an accelerator to selected ones of a plurality of patient treatment stations, each having a rotatable gantry for delivering the proton beam at different angles to patients supported in fixed orientations at the stations.

Especially for heavy ions that means ions heavier than protons a person skilled in the art tries to avoid the application of a rotatable gantry due to the difficulties to rotate heavy and huge equipment. A review about these systems avoiding rotatable gantries for heavy ions is published by E. Pedroni: Beam Delivery, Proc. 1st Int. Symposium on Hadrontherapy, Como, Italy, Oct. 18–21, 1993, page 434. Such systems known by a person skilled in the art need to move the patient in order to reduce either weight or size of rotated equipment. Some designers prefer a set of fixed beam lines instead of a rotating structure like it is known from the paper M. M. Kats, K. K. Onosovski: Instruments and Experimental Techniques Vol. 39, No. 1, 1996, page 1 to 7 and page 1 32. Therefore, it is obvious for a person skilled in the art to design an ion beam therapy system with heavy ions as an excentric system.

Excentric systems have, however, the drawbacks that radiation oncologists do not prefer such solutions since they clearly want and demand an isocentric system.

From the article by Marius Pavlovic in Nuclear Instruments and Methods in Physics Research, Section A, Oct. 11, 1997, Elsevier, vol. 399, no. 2–3, pages 439–454 a gantry design is known for light ions (Z=1–8), comprising superconductive dipoles as bending magnets excluding any edge focusing effects for these superconductive dipoles.

From the article by J. Pawelke et al. in Physics in Medicine and Biology; February 1996; IOP Publishing; Vol. 41, No. 2, pages 279–296 different cameras for in-beam position emission tomograph imaging are known for in situ and in vivo treatment plan verification and beam monitoring as well as dose control during heavy-ion tumor therapy.

From the article by P. Forck et al. in EPAC96, Fifth European Particle Accelerator Conference, Sitges, Spain; Jun. 10–14, 1996, Pages 2644–2646 a scintillator based halo-detector for beam position monitoring is known, used for the cancer therapy. This detector provides informations on the centre-of-mass, the width and the intensity by a sensitive nearly non-destructive method.

It is an object of the present invention to provide an ion beam therapy system and a method for operating the system according to the preamble of independent claims which keep the isocentre fixed with respect to the well defined room coordinate system and which makes the routine patient positioning and checking of the treatment angle easier. Further, the ion beam therapy system should provide a single plane configuration, which requires less bending but leads to a larger gantry length in contrast to the known isocentric "Cork screw" gantry concept known from A. Koehler: U.S. Pat. No. 4,812,658, Mar. 14, 1989 and S. Z. Rabin et al.: Nucl. Instr. and Meth. B40/41 (1989) page 1335. Therefore it is an aspect of the present invention to reduce also the gantry radius which normally becomes quite large for an isocentric geometry designed for a single plane configuration for ion beams particularly for a heavy ion beam.

Further, it is an aspect of the present invention to avoid the inaccuracy and the uncertainty of an out-beam positron emission tomograph. The positron emission tomograph patient is presently recorded after the irradiation. In this case the patient has to be first transported from the treatment room to the positron emission tomograph. During this time, the original distribution of the positron emitters (mainly $^{11}C$ and $^{10}C$, $^{13}N$, $^{15}O$) may be significantly deteriorated due to the transport and exchange of matter in the body. This should be avoided with the ion beam therapy system according to the present invention.

Another aspect of the present invention is to monitor the raster scanned ion beam particularly to monitor the raster scanned heavy ion beam after passing the last bending magnet. To measure and control the particle fluence and the beam position with high speed.

The object of the present invention is solved by the features of the subject matter of independent claims. Feature of preferred embodiments are defined with dependent claims.

An advantage of the present invention is that this ion beam therapy system has the possibility of controlling the charged particles by means of magnetic fields. Thanks to that, well focused pencil-like beams of charged particles with an adjustable spot-size can be formed and scanned over the treatment field following Kreisel the tumor contours. By a Variation of the scanning speed and the beam intensity any desired dose distribution within the target volume can be generated with a minimum extra dose delivered to the healthy tissue. The dynamic scanning beam delivery according to the present invention is an ideal technique for 3D-conformal tumor irradiation.

The ion beam therapy system of the present invention has the advantage of a clearly isocentric system with a reduced gantry radius, since the scanning system is located upstream the last bending magnet of the gantry. This position of the scanning system has the additional advantage of a high flexibility of the ion-optical system of the gantry, which can achieve an accurate control of the beam size and dispersion at the isocentre. By means of the edge focussing effect at the entrance and the exist edge of the last gantry magnet the parallel scanning mode is achieved. Advantageously, the resulting gantry configuration is a single-plane isocentric gantry with upstream location of a two direction magnet scanning system.

In a preferred embodiment of the present invention the ions of said ion beam are one of the group helium, carbon or oxygen ions. These carbon ions are very effective in treating patients with cancer disease. Since they have favourable physical and biological properties which can be exploited for developing improved treatment techniques in comparison to conventional proton beams, ion beams of carbon offer a unique combination of several advantages, firstly high physical selectivity, secondly higher biological effectiveness, third possibility of the irradiation verification with the aid of positron emission tomography. In the case of ions heavier than protons the favourable physical selectivity is enhanced additionally by a higher biological effectiveness which is an important advantage for the treatment of proton resistant tumours. By the proper selection of the ions species like carbon, the biological effectiveness can be controlled in such a way, that it remains low in the plateau region of the bragg curve and is elevated in the bragg-peak region. This enhances the peak to plateau ratio in terms of biological dose and enables to deliver a higher biological dose to the tumour while minimizing the dose to surrounding healthy tissue. The drawback of a proton beam is that it has only physical selectivity effect. While the radiation with high physical selectivity and additionally higher biological effectiveness is represented by carbon ions as a typical preferred embodiment.

Another preferred embodiment of the present invention has a gantry which further carries a positron emission tomography camera oriented towards an in-beam position. When the beam penetrates through the tissue, positron emitting isotops are generated by nuclear fragmentation of the primary ions. Some of these positron emitting fragments which differ from the primary particles just by the loss of one ore two neutrons (e.g. $^{11}C$, $^{10}C$ in the case of carbon ion beam) stop nearly in the same region as the primary particles. The stopping point of a positron emitter can be identified with the aid of positron emission tomography. With this preferred embodiment the positron emission tomography can be applied even during the irradiation. In this preferred embodiment the localisation can be advantageously monitored in-situ and the correctness of the irradiation procedure can be verified without an additional exposure to radiation.

In a further preferred embodiment the accelerator system comprises a linear accelerator most preferably a radiofrequency quadrupole (RFQ) and an interdigital H-type structure linear accelerator and a synchrotron accelerator. The advantages of this combination of accelerators are well known for an application to treat cancer with an ion beam. This compact and cost efficient RFQ/IH combination is provided for the first time in the present invention.

In a further embodiment said ion beam therapy system comprises means of monitoring the raster scanned beam after passing the last bending magnet. With this monitor system a precise measurement and a controlling of particle fluence and of beam position is possible with a high speed within the gantry area. The last bending magnet of the gantry is preferably a bending magnet for a bending angle of more than 60°.

Preferably, the monitoring means are mounted in-beam to a common support at the gantry exit.

In a further preferred embodiment said monitoring means comprise parallel-plate-ionisation chambers and multi-wire proportional chambers. This has the advantages that the particle fluence is measured by the parallel-plate-ionisotian chambers and the beam position and width of the beam is measured by multi-wire proportional chambers wherein the whole system can consist of three parallel plate ionisation chambers and two multi-wire proportional chambers. Two of these parallel plate ionisation chambers are used to monitor the particle fluence and the two multi-wire proportional chambers determines the beam position. The third ionisation chamber is advantageously independent and serves as an diverse safety device.

Further features, advantages and applications of the present invention are now illustrated by the further description of preferred embodiments in respect to the accompanying drawings.

FIG. 1 shows the layout of the building.

The facility shown in FIG. 1 is provided to use the ion beam therapy system and the method for operating the system according to the present invention.

The facility is a dedicated hospital-based cancer therapy facility. The building to be built for the centre has several important issues:

No constraints originated from fitting to existing rooms.

Custom-tailored building design taking into account an optimal patient flow.

Selection of a suitable site.

The building fulfills the following requirements:

a) Comfortable and friendly environment for the patients

The patient perceives a normal and friendly hospital environment without the technical laboratory-like background, accordingly the patient support is designed as a couch.

b) Preservation of the common standards of radiotherapy departments

The building is clearly subdivided into the medical and the accelerator parts in order to arrange the medical part similarly to conventional radiotherapy departments and to optimise the accelerator part according to the machine design.

c) More treatment rooms with identical properties

The patient flow will be speeded up if no restrictions exist that a given patient must be irradiated in a particular treatment room. That is why two identical gantry rooms exist. Another advantage of an arrangement according to FIG. 1 is that in the case of any problems with the equipment in one treatment room the fractionation schedule for a given patient can be maintained by using the other treatment room.

d) Easy access to the accelerator part for equipment installation and maintenance The accelerator area can be accessed by bulky equipment and instrumentation for installation, maintenance and repair purposes without obstructing activities in the medical part.

Figure 1A:
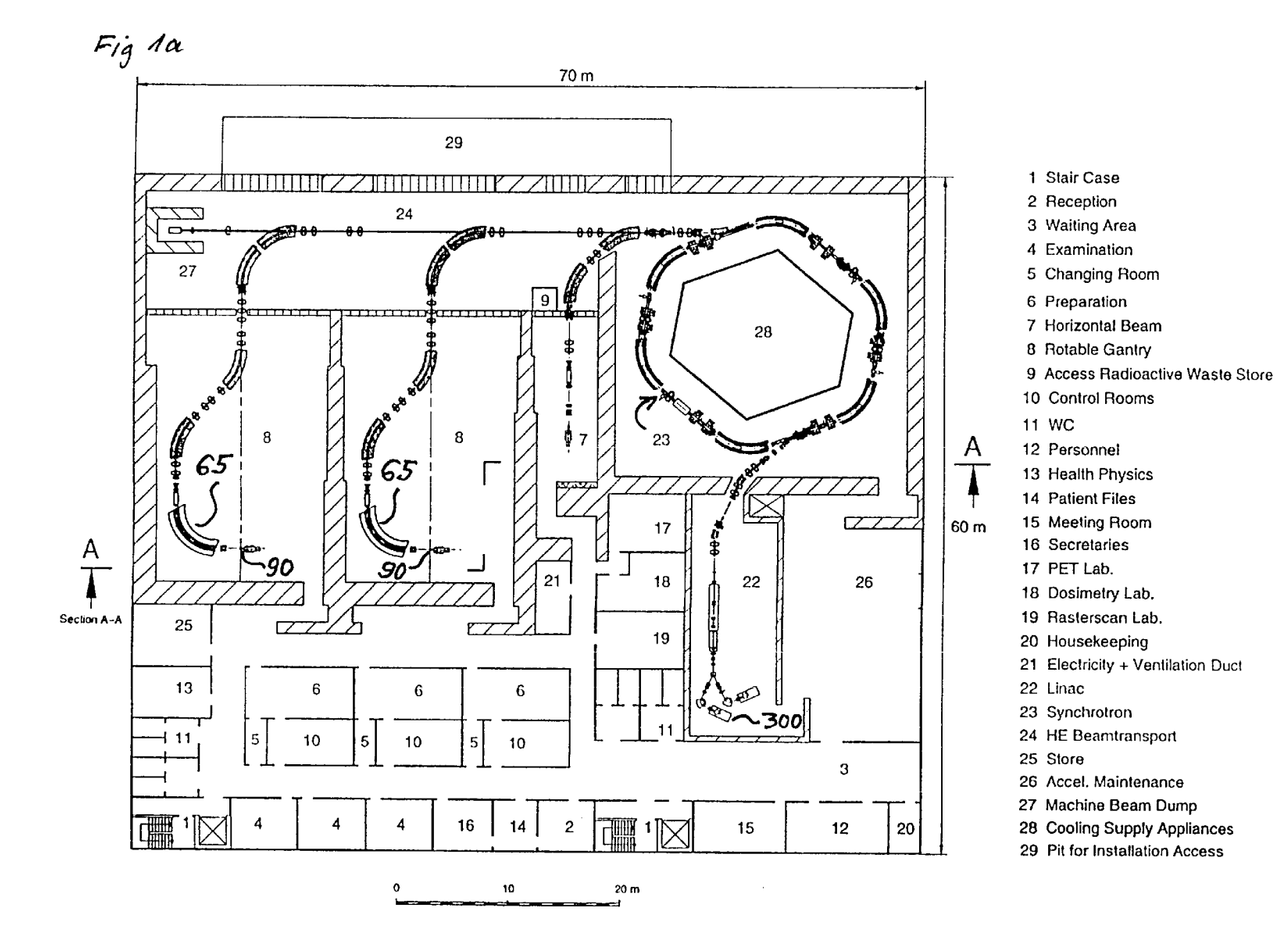
FIG. 1a is a partially cut plane view of an embodiment of the present invention.
Figure 1B:
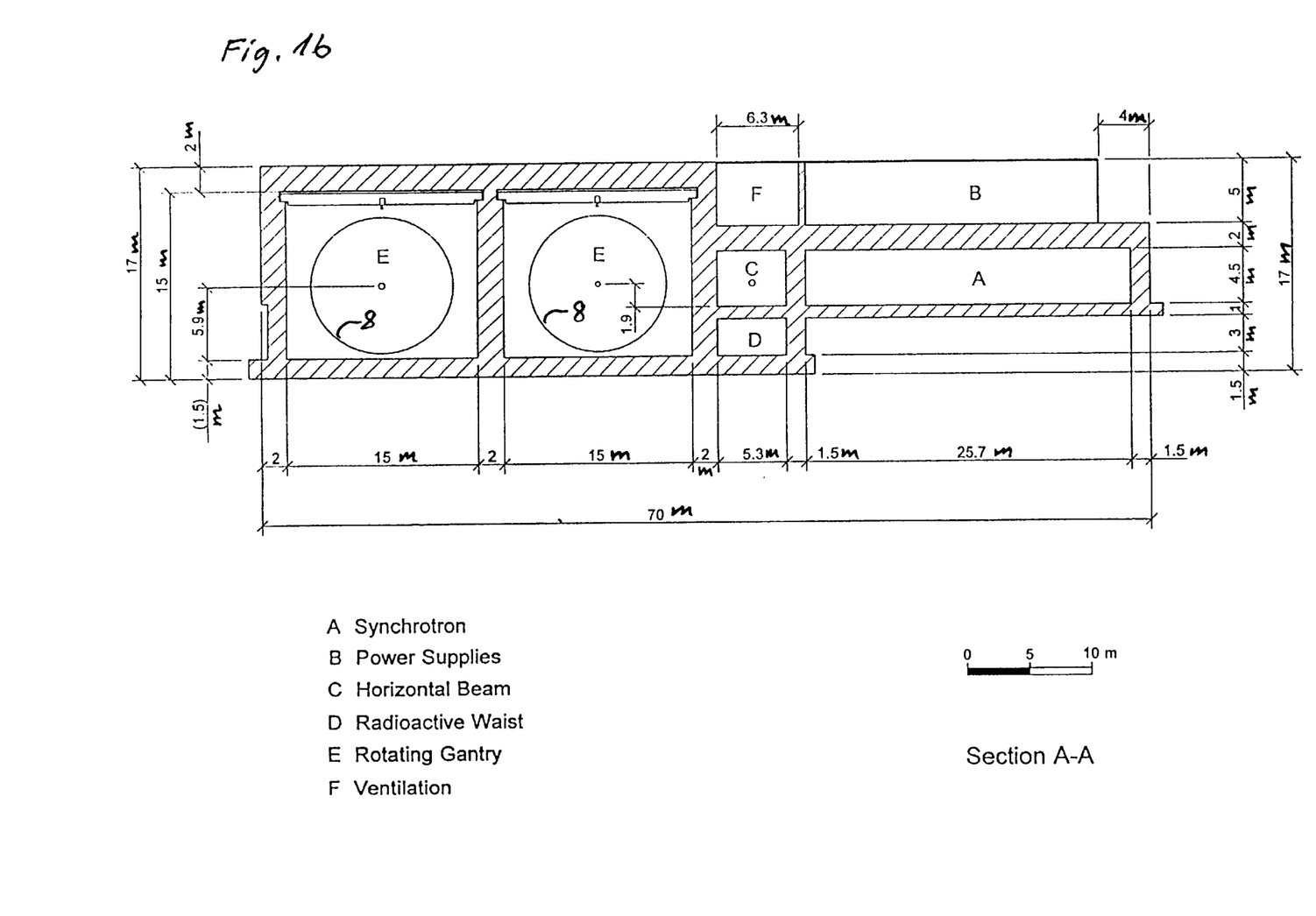
FIG. 1b is a vertical cross-section view of an ion beam therapy system.

The building layout of the irradiation facility including the accelerator system is sketched in FIG. 1. In the horizontal plane, the patient flow from a reception area to examination offices, preparation and treatment rooms was the guiding line. The accelerator and beam transport lines were accommodated accordingly. FIG. 1a shows the patient irradiation floor which contains the rooms relevant to the patient irradiation procedure and houses the accelerator. The technical control rooms for three treatment places are located on this floor as well as a few laboratories for dosimetry, PET, accelerator maintenance, etc. On the second floor which is guided by the large space requirements of the gantry rooms, the power supplies of the accelerator and the irradiation equipment, the air cooling facilities and further offices will be accommodated. An accelerator control room which only will be entered in running-in period and trouble diagnostic interventions is incorporated in the power supply area. A water cooling machinery for 3.5 MW power is placed inside the synchrotron ring, cooling towers and main transformers are expected to be located outside the building on the synchrotron top level. The irradiation floor is placed underground. Therefore outside access pits and an overhead crane have to be provided, which results in an increased story elevation of 1.5 m. FIG. 1b shows a vertical section of the building.

The shielding precautions against fast neutrons ($\geq 100$ MeV). originating from interaction of the high energy carbon beam with patient body, cannot easiliy be based on the maximum dose rate outside the shielding walls, rather than on the accumulated dose of the personnel over one year. The energy of the carbon beam is folded in by a probability factor of 5 and the intensity by a factor of 1000.

The facility, shown in FIG. 1, is the first facility for using the ion beam therapy system and the method for operating the system according to the present invention, which operates in such a large span of beam parameters.

Since the option of further stories on top of the gantry rooms must be maintained for office use, the top shielding of the gantry rooms are determined carefully from the beginning taking into account also the irradiation of the patients from the bottom. Therefore the counterweight of the gantry is put on the opposite side to the exit of the last gantry dipole which functions as the last bending magnet. In this position, the counterweight can serve also as a shielding against the fast neutrons. The walls and the ceiling of the irradiation rooms will be cast from 2 m concrete. This thickness is adequate for screening the neutrons coming out from the target under 90° angle and passing by the counterweight shielding of the gantry.

Figure 2:
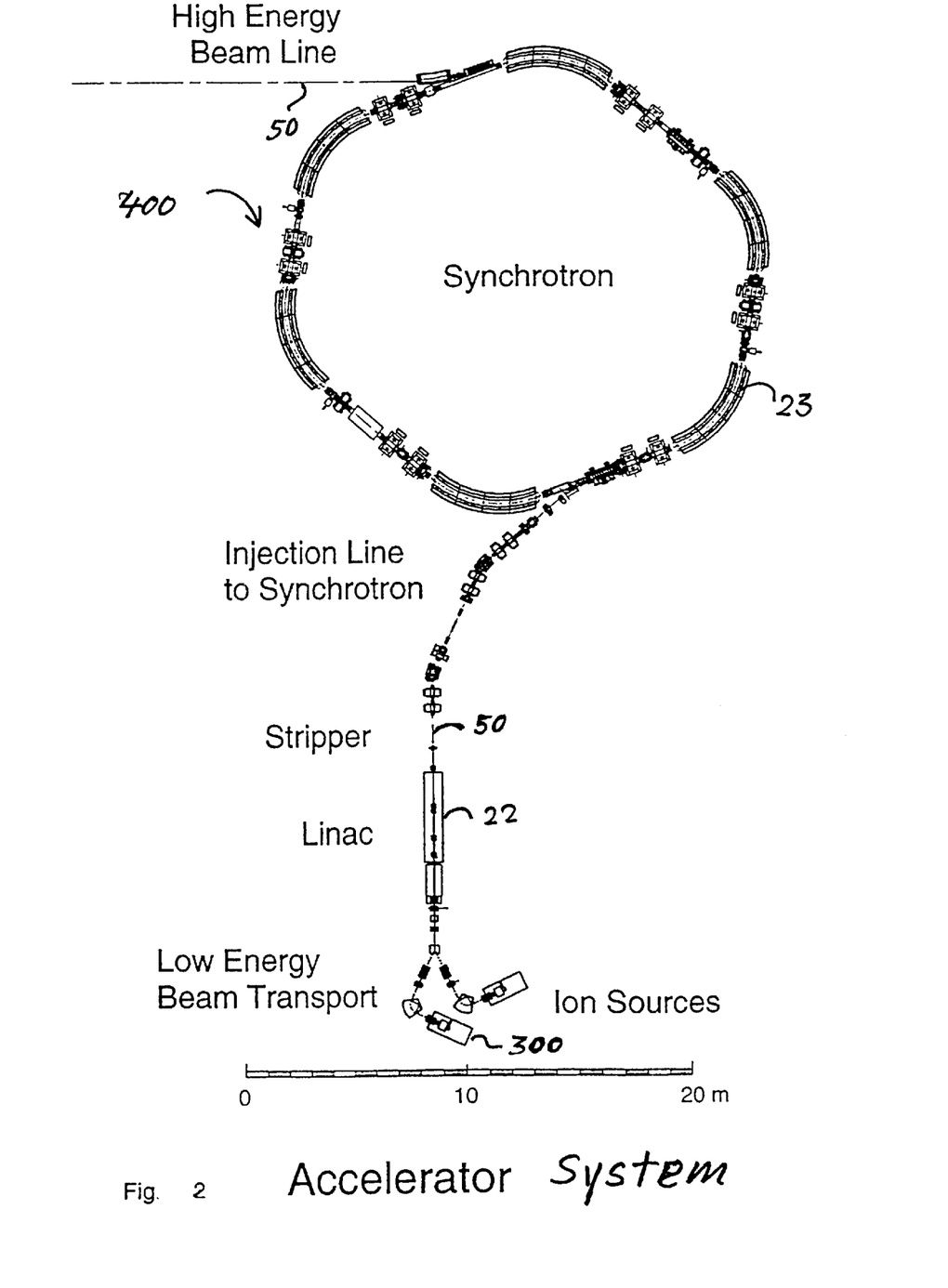
FIG. 2 is a plan view of an accelerator system for an embodiment of the present invention.

The accelerator system is shown in FIG. 2 and its main parameters are collected in Tab. 1.

Figure 3:
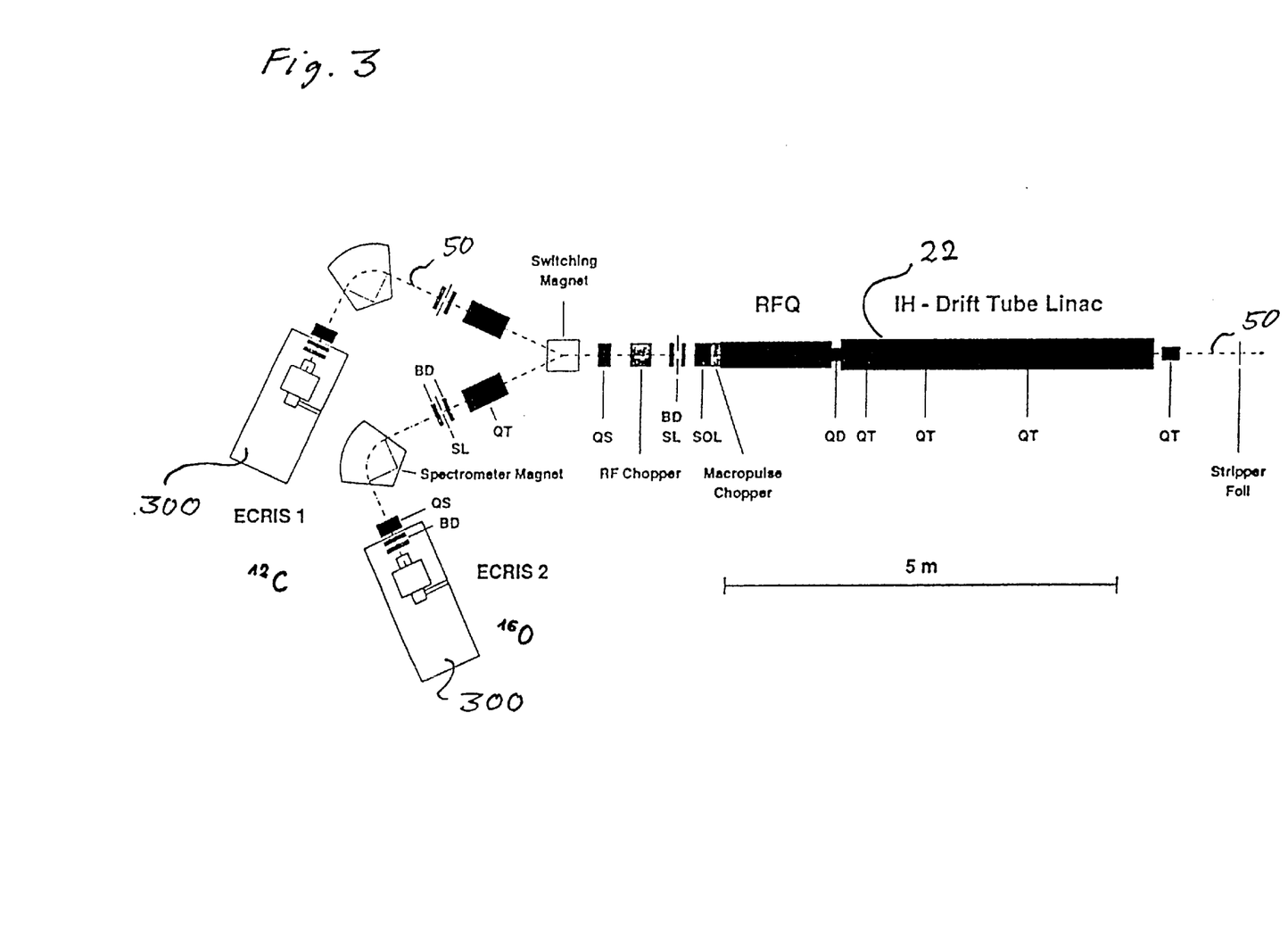
FIG. 3 is a plan view of a low energy acceleration part of the accelerator system.

The injection chain, shown in FIG. 3, consists of ion sources, a low-energy beam transport line, a Radio-frequency Quadrupole (RFQ), an IH linac and an injection line into the synchrotron. Its main features are:

To create and to analyse beams of desirable particles.

To monitor beam contamination.

To control the beam intensity.

To accelerator the beam up to the injection energy of 7 MeV/u.

To define the length of the pulse injected into the synchrotron.

To match the synchrotron injection requirements.

The injection chain shown in FIG. 3 consists of two ion sources and two low-energy beam transport branches, the switching magnet, the RFQ and the linac, and the stripping foil, wherein the abbreviations are as follows: ECRIS=Electron Cyclotron Resonance Ion Source, BD=Beam Diagnostic block, QS=Quadrupole Singlet, QD=Quadrupole Doublet, QT=Quadrupole Triplet, SOL=Solenoid, SL=Slit collimator. The total projected length of the injection chain is about 13.5 m.

There is one aspect of this embodiment not usually relevant in case of beams for physics experiments. The therapy beam must not contain contaminations of ion species with atomic numbers Z differing from the wanted Z number in intensity fractions by more than 1%. This is a problem for heavy ions, because the accelerator chain and the subsequent beam transport elements are selective only to the charge over mass ratio. This ratio is the same (Q/A=1/2) for a dozen of heavy ion species at the highest charge state. This problem is solved by extracting a lower charge state from the ion source with a minimum probability of an ambiguous charge over mass ratios equal to the charge over mass ratio of the desired ion. This requirement has a preference over the highest charge states. In order to minimise the contamination probability, $^{12}C^{4+}$ will be extracted from the ion source. There remains a coincidence in charge over mass ratio Q/A=1/3 for example for isotopes $^{18}O^{6+}$, $^{24}Mg^{8+}$, $^{27}Al^{9+}$, or $^{36}Ar^{12+}$. Some of them ($^{18}O^{6+}$, $^{27}Al^{9+}$) are eliminated downstream the stripper because of having charge over mass ratio different from 1/2 after being fully stripped. However, a coincidence Q/A=1/2 remains for $^{36}Ar^{18+}$ and $^{24}Mg^{12+}$. The first one has a negligible fraction in air (supplied by adsorption or leaks in the source). The second one is avoided by selecting properly analysed material for the source construction.

For He ions, where the charge state $He^{2+}$ is mandatory when the linac is designed for $^{12}C^{4+}$, the contamination problem persists for $^{16}O^{8+}$. The provided solution is to use $^{3}He^{1+}$ isotope which has the same Q/A=1/3 as the $^{12}C^{4+}$.

The currents which have to be extracted from the ion source depend on the required beam intensities at the patient taking into account all beam losses along the accelerator chain. For $C^{4+}$, an electrical current of 120 $\mu A$, for $H^{2+}$, 600 $\mu A$ and for protons 1.2 mA will be delivered by the ion source in the DC mode. These DC beam currents can be delivered by an ECR ion source in a stable, reproducible and reliable operating mode particularly by the source models using permanent magnets as used in this embodiment.

The design of the low energy beam transport line shown in FIG. 3 is largely affected by the fact that different particle species are going to be delivered by the common accelerator complex. Availability of different particles is meant not as an option, rather than as an equivalent operational feature, switchable in short time intervals less than one hour. Following the recommended extraction voltages of the ECR ion source extraction system, the injection energy to the RFQ is set to 8 keV/u for all particle species. This value is also convenient from the point of view of reducing the space charge effect in the case of proton beam. Availability of different particle beams in the switchable mode requires a source strategy, where the carbon and the proton ion source are running all the time in parallel. Considering the proton ion source for low-LET irradiation as well as a substitute for the regular carbon source in case of a failure, two identical branches consisting of ion source and spectrometer line are provided in this embodiment. These two branches feed the beam line into the RFQ through a switching magnet.

The spectrometer optics are designed not only to separate the charge states coming out of the source, but also to identify the impurities. Though, by nature, the magnetic spectrometer can not discriminate impurities having the same charge over mass ratio as $^{12}C^{4+}$, it can give a hint on beam contamination by scanning adjacent charge states and isotopes of possible contaminants. In the straight line to the RFQ, which is optically determined by beam matching properties, two other devices are inserted. First, a macropulse chopper which cuts out of the ion source DC beam nearly representative beam pulses for injection into the synchrotron. The fine pulse shaping is done by an additional chopper in the injection line between the linac and synchrotron ring. The macropulse shaping is advisable because the sources are running in the DC mode for the sake of stability and for allowing a stationary space charge compensation in the low energy beam line, which is essential for a proton beam.

Another important subsystem, incorporated in the low energy beam line, is an RF chopper as a fast intensity degrader, never considered in equivalent equipments in beam therapy system so far. The RF chopper controls the intensity of the beam injected into the RFQ over the ratio $I_{max}/I_{min}=1000$ keeping the transversal beam emittance constant and well matched to the RFQ acceptance. This solution has an advantage (compared to other possibilities like transversal beam defocusing and cutting out by slits) that the beam emittance does not depend on the beam intensity.

The linear accelerator (or linac) shown in FIG. 2 and 3 consists of an RFQ section from 8 to 300 keV/u and an IH section providing the essential acceleration from 0.3 to 7 MeV/u. From considerations of length shortening, a high operating frequency of 216 Mhz is applied to shorten the length of the system. Detailed beam dynamic simulations have been performed to optimise the design of the accelerating structure. An 1:2 scaled RF model is used to verify the dimensioning of the IH structure.

Figure 4:
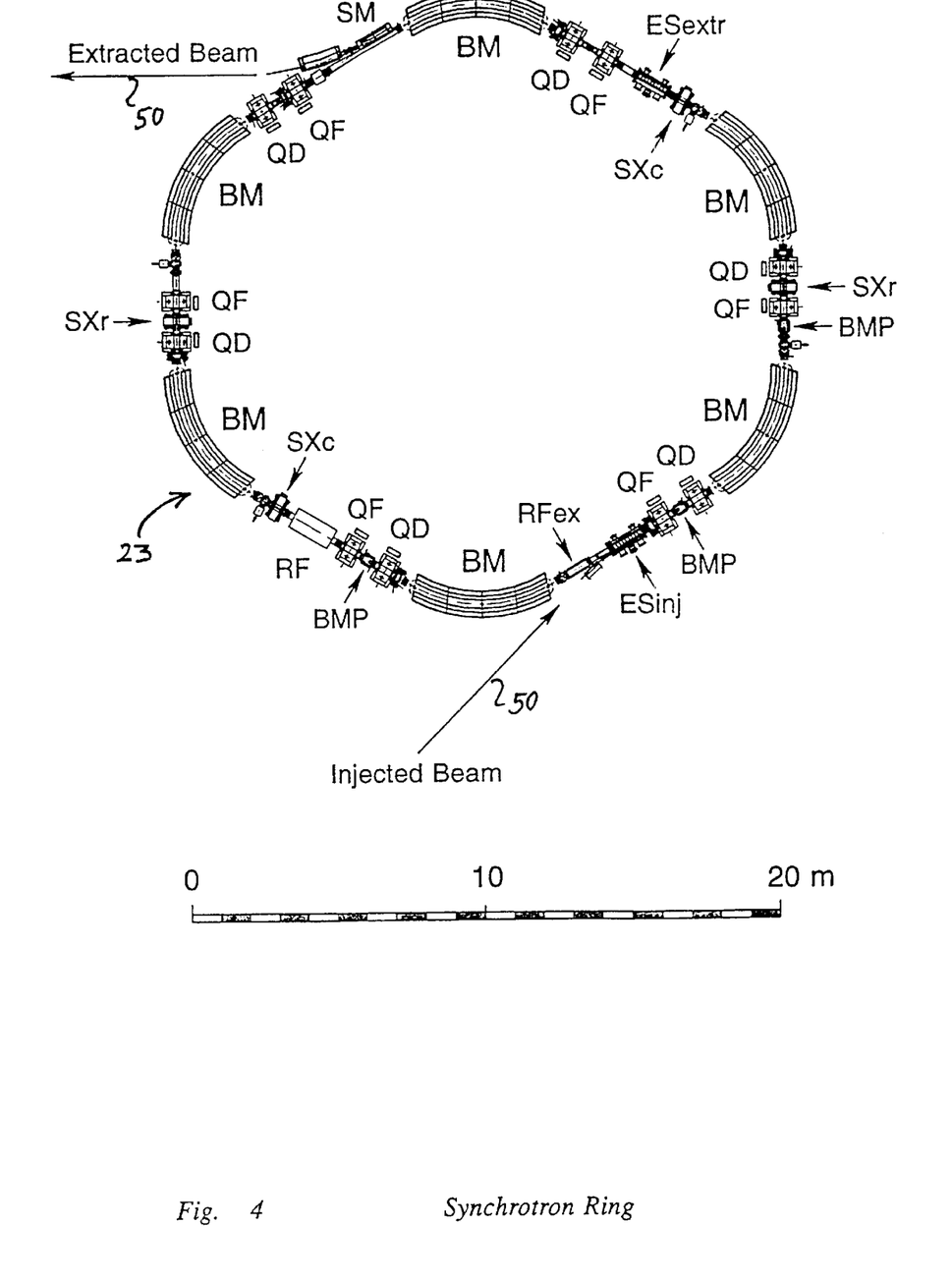
FIG. 4 is a plan view of the synchrotron ring.

The injection line to the synchrotron shown in FIG. 2 and 4 (approximately 16 m long) contains a stripper target, a chopper system for shaping the injection pulse, dipole magnets for charge over mass analysis, quadrupoles for matching the beam emittance to the synchrotron acceptance, beam diagnostic equipment, and finally an inflector magnet. The subsequent electrostatic inflector is a part of the ring components.

The stripper target consists of carbon foils, 5 selectable units being mounted on a ladder. The foil thickness is about 50 $\mu g/cm^2$ and the lifetime of an individual foil is about 6 weeks. The stripping efficiency $C^{4+} \rightarrow C^{6+}$ is better than 80% at 7 MeV/u. A gas stripper with its inherent feature of infinite lifetime is not mandatory for the low beam intensities involved and hence is an unnecessary cost item. The focal beam spot on the foil is about 2 mm, the emittance increase due to multiple scattering stays below 5% and the contribuation to the momentum spread of the linac output beam of $\pm 1.5 \cdot 10^{-3}$ before stripping is in the order of $\pm 5 \cdot 10^{-4}$.

The injection chopper, a pulsable electrostatic deflector with two small DC bending magnets, cuts out of the 0.2 ms linac pulse the injection pulse with a length of about 30 $\mu s$ corresponding to the requested number of 15 injection turns. The number of turns can in principle be chosen according to the intensity requirements. However, it is not proposed to use this property dynamically because the emittance of the extracted beam would change, which consequently would require a retuning of the high energy beam line and the gantry optics.

The injection beam line into the synchrotron includes furthermore 6 quadrupole lenses for matching the β-function and the dispersion function of the ring. Steering magnets and emittance defining slits are foreseen, as well, along with appropriate diagnosis for beam current, beam profile and beam position. The beam parameters at the exit of the injection chain are listed in Tab. 2.

The main features of the synchrotron are:
Multiturn injection means for the ions.
Acceleration means of the ions to a desirable energy.
Pulse-to-pulse energy variation means.
Slow beam extraction means with variable extraction time.

The injection procedure was chosen in favour of the multiturn process. It is in use at the SIS without any complication as well as at the HIMAC light-ion medical synchrotron. In this approach the demand on ion source and linac performance can be kept to moderate values with ample reserve for ion source performance and linac mistuning. The geometrical demand on magnet aperture is only modestly determined by the multiturn approach as the horizontal aperture of the ring magnets is determined mainly by the resonant extraction process.

For the component layout of the ring it was a guiding incentive to keep the number of components low because failures occur frequently at water hoses and current connections. Therefore, six 60° bending magnets have been chosen. The manufacturing of the 60° dipoles has to be verified in a pre-production model. The quadropoles and sextupoles have not to be subject to prototyping procedures. The synchrotron ring components are listed in Tab. 3 and the ring layout is depicted in FIG. 4.

For cost optimisation reasons, a conservative maximum flux density of 1.5 T was chosen for the dipole magnets. Here a time of 0.5 sec for the magnet ramp was chosen between the end of the injection and start of the extraction corresponding to a ramping rate of 2.46 T/s allowing for a decently save wall thickness of the solid vacuum chamber in the magnets.

A mean pressure of $10^{-9}$ Torr for the ring vacuum meets the requirements. This level can be accomplished without baking procedures when the components are treated properly before installation. Lifetime measurements of a $C^{6+}$ beam supports this choice. Sputter ion pumps are foreseen exclusively. The bake out of the ring vacuum is of a persistent concern in other projects, with the argument that the base pressure can rapidly be reached after a leak cleaning procedure if the system can be baked out.

The extraction energy is selectable in the pulse-to-pulse mode between 50 and 430 MeV/u, the latter energy corresponds to a penetration range of the carbon beam in water of 30 cm and results in a maximum beam rigidity of 6.6 Tm. The maximum magnetic rigidity is a cost-driving factor for the ring and the subsequent beam transport hardware.

For beam extraction, the 'resonant' slow extraction procedure is provided. This slow beam extraction mode is necessary for the raster scanning beam delivery technique in order to provide enough time for tumour painting as well as for beam monitoring.

The emittances of the slowly extracted beams are relatively small. Their values depend upon the beam properties at injection, the extraction beam energy, the extraction procedure and the synchrotron settings before the extraction starts. Although the horizontal and vertical emittances are in general different, the demands of a stable, symmetrical and 'round' beam at the treatment place can be fulfilled with an appropriate setting of the beam optics in the beam transport line.

In order to use the beam spills as effectively as possible, a variable extraction time from 1 to 10 seconds is provided. Without this feature, a large amount of the treatment time would be wasted between extraction interruption (completion of a tumour slice) and a new machine cycle. In the case of variable extraction time, a new machine cycle can immediately be started after the extraction corresponding to a given tumour slice has been finished. The feature is therefore important to minimise the treatment time. Another feature of the extraction technique is a fast switching off—and on the extraction during the same synchrotron cycle (i.e. the same beam energy). This possibility is expected to be useful in two situations. The first, when an irregular tumour shape together with tissue inhomogeneities results in a tumour isoenergy slice consisting of several insulated 'islands' with the areas in between where no dose should be deposited. The second, when a respiration gated irradiation is performed.

A major impact on the synchrotron design and the choice of the extraction technique are the requirements of the raster scan method with a reliable fast spill abort, and a time optimised and, if necessary, respiration gated irradiation.

For the raster scanning beam delivery method, a smooth time structure of the extracted beam spill is desirable. At the resonant extraction mode, this time structure is ususally not uniform but has a noisy structure. A minimisation of these intensity fluctuations can be achieved by various means, e.g. ripple reduction of the synchrotron power supplies, installation of a feed back system, etc. The tight tolerances of the dose distribution over the tumour volume can reproducibly be achieved in this embodiment of the present invention.

Technically, the slow extraction can be realised by varying the beam optical setting of the synchrotron ring by shifting the momentum of the beam or by exciting the amplitude of the particles. The RF knock-out extraction is presently provided for the synchrotron of this embodiment of a therapy system as this method satisfies all the above described requirements and no ion-optical variations of the ring have to be performed on the extraction level.

An important issue affecting the design of the subsequent high energy beam transport system and the gantry in particular is that the emittances of the extracted beam are expected to be different in horizontal and vertical planes.

Figure 5:
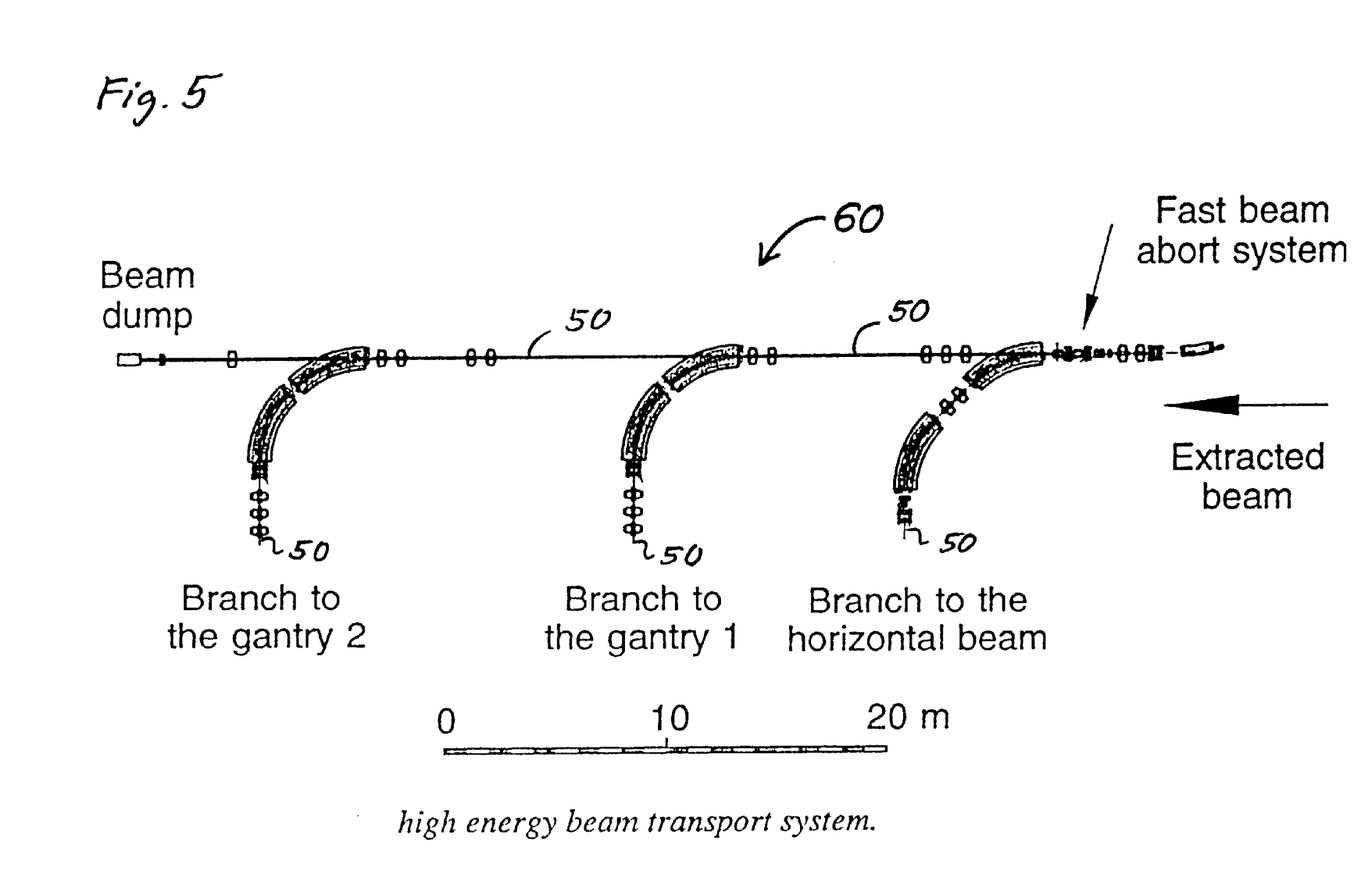
FIG. 5 is a plan view of a high energy beam transport system.

The High Energy Beam Transport system (HEBT) shown in FIG. 5 transports the extracted beam from the synchrotron to the treatment rooms and participates on forming the final beam parameters at the isocentre. In the new facility, one fixed horizontal beam line and two gantry treatment rooms are provided. In the case of the fixed horizontal beam line, the HEBT system is fully involved in the final beam tuning providing the achromatic beam transport from the synchrotron to the isocentre and control of the beam spot-size at the isocentre (from 4–10 mm beam). These parameters must be achieved at all beam energies taking into account the energy-dependance of the beam emittance as well as the different beam emittances in horizontal and vertical planes.

In the gantry treatment rooms, the HEBT system is not involved in the final beam tuning rather than in forming a suitable beam at the gantry input. The point of connecting the rotating gantry to the fixed beam transport line—the so called 'coupling point'0 is defined to be the gantry input. Desirable ion optical properties at the gantry input are:

Achromatic beam transport from the synchrotron to the coupling point.

Beam waists in both planes.

Equal beam size in horizontal and vertical planes.

The final control of the beam parameters at the isocentre is then performed be different settings of the gantry ion optical system.

The HEBT System according to FIG. 5 consists of quadrupole lenses, bending magnets and beam diagnostic devices. Following the extraction septum magnet, a fast beam-abort chopper is installed. It will be used in emergency situations whereas the switch-off of the beam after the completion of a raster scan slice will routinely be performed by interrupting the extraction procedure. The high energy beam lines must be demountable in order to have access to the gantry caves by an overhead crane in case of an intervention to the bulky machinery.

Figure 6:
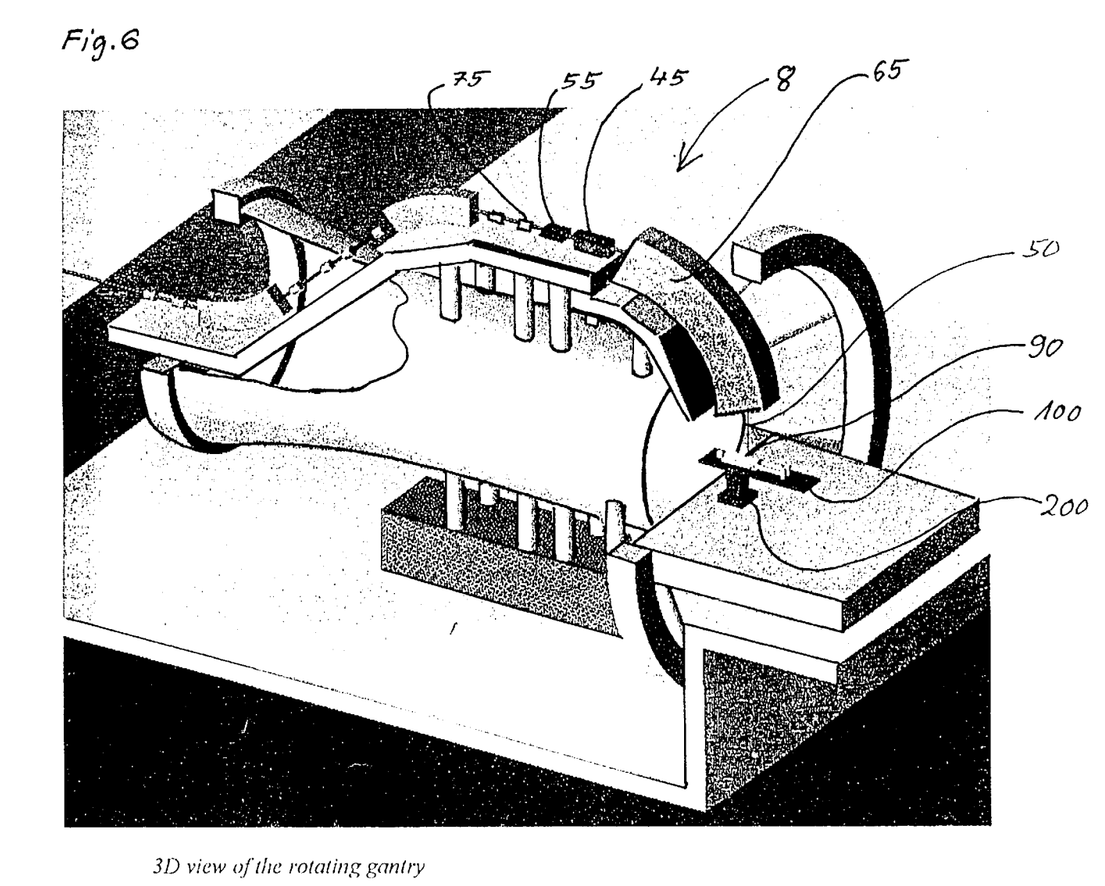
FIG. 6 is a perspective view of a rotatable gantry.

The gantry shown in FIG. 6 may be considered to be a part of the beam transport system as well as a sub-system of the beam delivery equipment. In any case, the gantry (8) is an outstanding part of the facility equipment and no gantry has been built so far for beams of particles heavier than protons. Heavy-ion gantries were traditionally assumed to be too expensive and too difficult to build. However, for a dedicated cancer therapy facility where a large spectrum of tumour sites is expected to be treated, a rotating gantry (8) is strongly recommended as it becomes evident from recent experience from proton therapy facilities. At present, 8 proton gantries are in operation or under commissioning world-wide and most of the new project proposals contain typically two proton gantry rooms for proton treatment of cancer.

For the present embodiment an ion-beam system for two identical rotating ion gantries equipped with a raster scanning system are provided. Such a combination provides the highest possible degree of flexibility and dose-to-tumour conformity. The gantries will be equipped by a PET camera for in-beam PET monitoring of the irradiation procedure.

For beam optics reasons, the scanning system is preferably placed behind the last quadrupole lens (75) of the gantry (8) and in front of the last-gantry dipole magnet (65). In this position, a high flexibility of the ion-optical system of the gantry can be achieved to control the beam size and dispersion at the isocentre. The scanning system (45, 55) consists of one horizontal (45) and one vertical scanning (55) magnets and its parameters have been chosen to be identical (or close) to the system in the fixed horizontal beam line. By means of the edge focusing effect at the entrance and the exit edge of the last gantry magnet (65) the parallel scanning mode can be achieved. The resulting gantry configuration is a single-plane isocentric gantry with upstream location of a two-direction magnetic scanning system. FIG. 6 shows a 3D view of the gantry. The main gantry parameters are listed in Tab. 4.

One important part of this embodiment of a gantry (8) with an integrated raster scanning means (45, 55) upstream of the last bending magnet (65) is the last 90° gantry dipole which has to have a large aperture (in our case 24×22 cm) in order to allow for up-stream position of the scanning system. The present embodiment is using the maximum flux density in the magnet air gap of 2 T. This value has also been used for the beam transport design of the gantry and the gantry dimensions in Tab. 4 correspond to the 2 T magnet, too. However, the gantry rooms of the system have been designed with a space safety margin to be able to accommodate slightly larger gantries if a detailed magnet design reveals a necessity to reduce the field down to 1.9 or 1.8 T. In such a case, the beam transport system of the gantry will have to be refined. However, this will not affect the gantry concept of the present invention.

Figures 7, 7A:
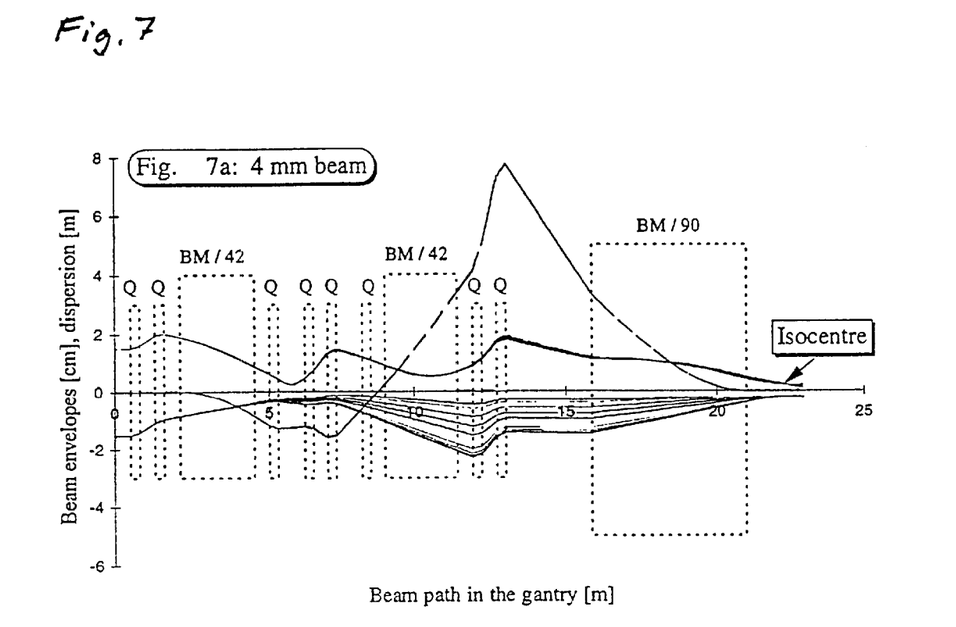
FIG. 7a is a diagram of a beam path in the gantry for a 4 mm beam.
Figure 7B:
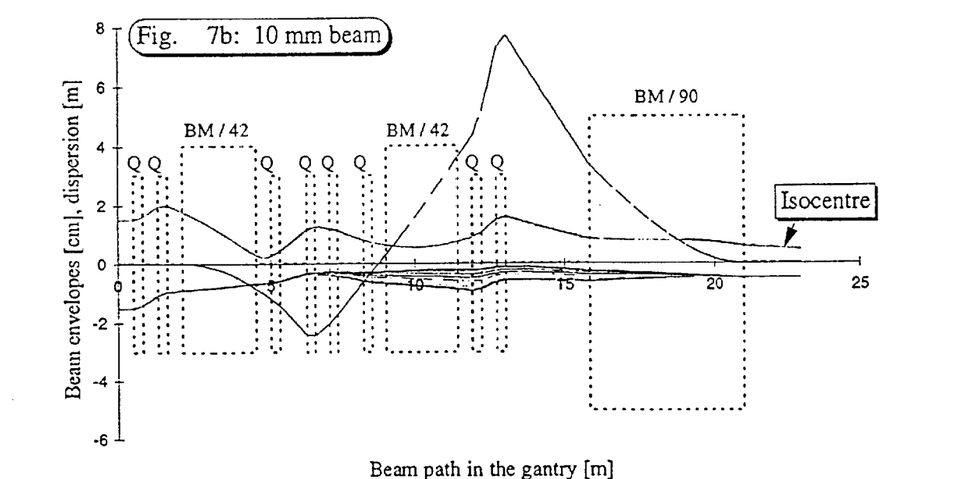
FIG. 7b is a diagram of a beam path in the gantry of a 10 mm beam.

For the functionality tests of the gantry ion optical system an input beam with horizontal emittance of $\epsilon_x=1\pi$ mm mrad, vertical emittance of $\epsilon_y=5\pi$ mm mrad, and momentum spread of 0.2% is provided. It has been checked that desirable beam parameters (circular beam with 4–10 mm spot size, achromatic beam transport) can be achieved for all angles of gantry rotation exclusively by proper tuning of the gantry optics as a function of the gantry angle without changing the setting of the high energy beam line. FIGS. 7a and 7b show the beam envelopes for 4 and 10 mm beams, respectively, and the angles of gantry rotation 0÷90° in 10° step.

FIG. 7 shows the beam transport through the gantry, wherein the abbreviations are as follows: BM/42=42° bending magnet Q=quadrupoles, dashed line=dispersion function. The upper and lower parts of each plot show the beam envelopes in the horizontal and vertical planes of the gantry, respectively, for different angles of gantry rotation.

An installation of the in-beam positron emission tomograph is preferred to the out-beam standard PET so that the highest possible accuracy of the PET record can be achieved. The PET image is taken directly during the irradiation. The most convenient occasion is using the time slots between the beam spills, when the PET signal is less obscured by a background noise compared to the periods with beam-on. In-beam PET requires a special configuration of the beam delivery system, patient table and the positron camera in order to avoid mechanical clashes between these systems as well as to provide ample space around the patient for patient positioning. That is why, the positron camera has to be laid out in a limited angle geometry. This requires the application of rather time consuming iterative tomographic reconstruction algorithms which becomes more feasible with the increasing performance of the computers regarding speed and storage capacity.

From the technical point of view, the raster scanning system consists of three main parts:

The scanning (sweeping) magnets.

The beam monitoring system.

The raster-scan control system.

The raster-scan control system is an integrated part of the overall control and safety system.

The basic function of the scanning magnets is to deflect the beam out of the optical axis and to sweep it over the treatment area in a path-pattern defined by the treatment plan.

In a preferred embodiment redundant safety means are provided, having the possibility of vertical and horizontal beam offsets. It means, that the non deflected beam by zero excitation of the scanning magnet passes not the isocentre and does not hit the patient.

The present embodiment of an ion-beam therapy system including a raster scanning system is the first and the only scanning system world-wide. It has been successfully tested and applied in the irradiation of human patients.

In a preferred embodiment a window frame design is chosen with a relatively low flux density to keep inductances low. The number of conductor windings is chosen in such a way as to have a relatively conservative relation between current and driving voltage. The conductor cross-section is small to avoid high eddy current losses due to the fast ramping rate. Tight tolerances are kept during manufacturing of the coils and during their final symmetric adjustment in the magnets. Insulation thickness of the finished coils is measured using an eddy current procedure according to DIN 50984. The front end edges of the poles are machined to have comfortable radii for the bent up coil ends. The conducting contacts between the sheets are removed by chemical etching.

Figure 8:
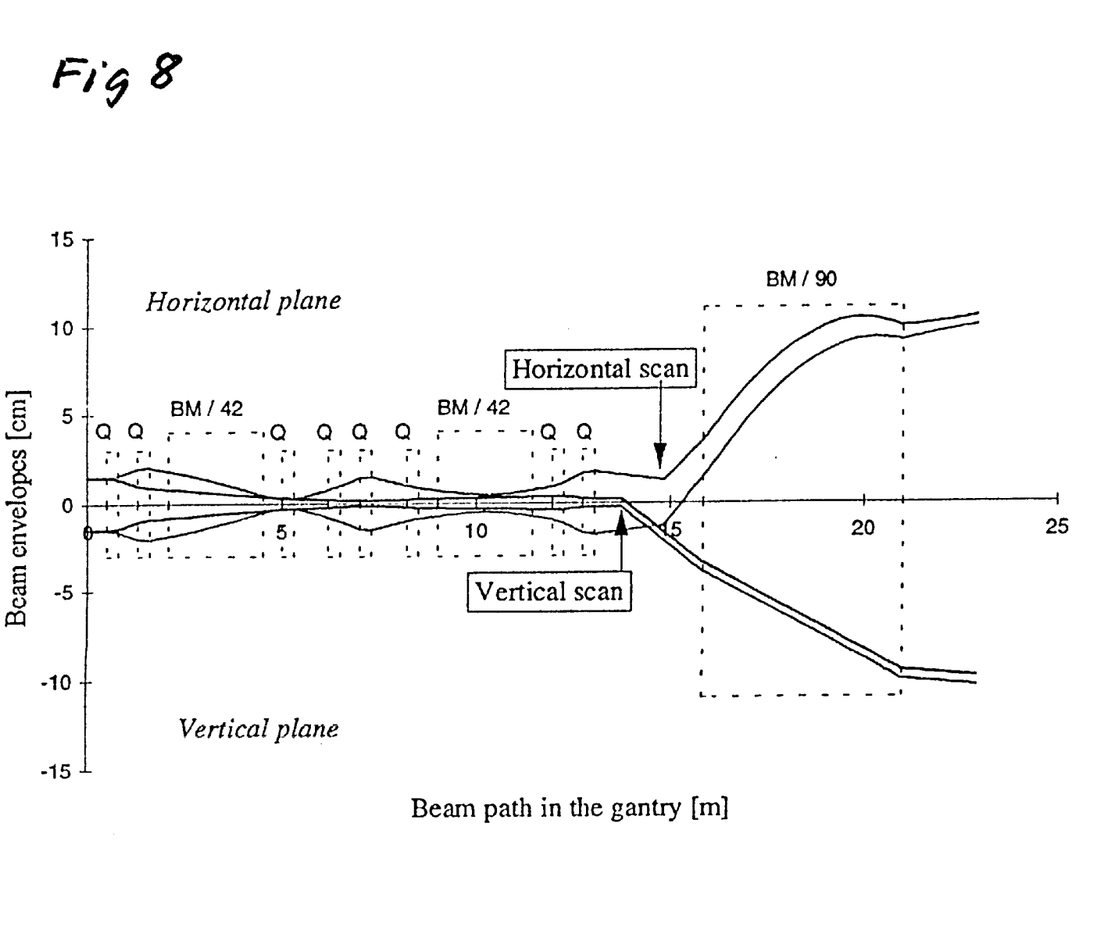
FIG. 8 is a beam path in the gantry showing the effect of horizontal and vertical scan.

At the current gantry design, the space has been reserved to accommodate a scanning system having the parameters of a scanning system presented in Tab. 5. FIG. 8 shows the beam envelopes of the scanned beam in the gantry. The action of the scanning magnets is simulated as an angular kick in the middle of the scanning magnets. Accuracy of this approximation is sufficient for the gantry design, as it has been verified by comparison with precise beam transport simulations.

FIG. 8 shows the beam envelopes of the scanned beam in the gantry, wherein the abbreviations are as follows: BM/42=42° bending magnet, BM/90=90° bending magnet, Q=quadrupoles. The deviation of the output scanned beam from the parallel scanning mode is currently about 0.1° and can be totally removed with a proper gantry design by optimising the angles of the pole face rotation and the position of the scanner magnets.

The treatment of patients with the raster scanning beam delivery technique requires precise measuring and controlling of particle fluence and beam position with a high speed. Therefore, another key-unit of the raster scanning beam delivery system is a beam monitoring system. The present beam monitoring system is able to measure the particle fluence every 12.5 $\mu$s and the beam position and width every 150 $\mu$s. The particle fluence is measured by Parallel-Plate-Ionisation-Chambers (PPIC) and the beam position and width by Multi-Wire-Proportional-Chambers (MWPC). The whole system consists of 3 parallel-plate ionisation chambers and 2 multi-wire proportional chambers mounted on a common support upstream of the patient couch (200) and downstream the last bending magnet (65). Two PPIC are used to monitor the particle fluence and two MWPC determine the beam position. The third ionisation chamber is independent and serves as a redundant safety device.

In a preferred embodiment all detectors are operated with a constant flow of $Ar/CO_2$ gas (mixture of 80/20 mass percentage) with 2 liters/h at atmospheric pressure. The high voltage is kept a +1000 V and +1600 V in case of the PPICs and MWPCs, respectively. To monitor the proper working conditions each chamber has been equipped with sensors for gas flow, pressure, temperature and high voltage. The readout, control and interlocking is done by newly developed electronics and software.

TABLE 1

The main parameters of the accelerator cancer therapy

| | |
|---|---|
| | Injector |
| | Ion sources |
| Number: | 2 |
| Type: | Electron Cyclotron Resonance Ion Source (ECR) |
| Model: | SUPERNANOGUN [81] |
| Operating frequency: | 14.5 GHz |
| Output beam energy: | 8 keV/u |
| Source currents (DC, e$\mu$A): | $\geq$120 ($C^{4+}$), 600 ($He^{2+}$), 1200 (protons), 300 ($3He^{1+}$) |
| Beam emittance (normalised): | <0.4 $\pi$mm mrad |
| Low energy beam transport (ion source - RFQ) | |
| two independent spectrometer lines: | 90° spectrometer dipole, 26.5° edge focusing, |
| | resolving power $\dfrac{m/q}{\Delta(m/q)} \approx 300$ |
| intensity variation: macropulse chopper | RF chopper |
| RFQ and intertank matching | |
| Components: | one tank, 4-rod structure |
| Input energy: | 8 keV/u |

TABLE 1-continued

The main parameters of the accelerator cancer therapy

| | |
|---|---|
| Output energy: | 300 keV/u |
| Operating frequency: | 216 MHz |
| Electrode length: | ≈1.2 m |
| Acceptance (transversal, normalised): | 1 π mm mrad |
| Tank diameter: | ≈0.3 m |
| Intertank matching: longitudinal | 2 drift tubes inside the RFQ tank [83] |
| transversal | 1 magnetic quadrupole doublet |

IH drift tube LINAC

| | |
|---|---|
| Components: | one tank, 58 gaps, 3 magn. quadrupole triplets |
| Input energy: | 300 keV/u |
| Output energy: | 7 MeV/u |
| Operating frequency: | 216 MHz |
| Acceptance: transversal, normalised: | 0.8 π mm mrad |
| longitudinal: | 1.5 π keV/u × ns |
| Tank length: | 4.0 m |
| Tank diameter: | ≈0.35 m |

Stripper section and the output beam parameters at the injector exit

| | |
|---|---|
| Stripping foil: | 50 μg/cm² carbon foil |
| Beam diameter on foil: | 2 mm |
| Ion species to synchrotron: | protons, $He^{2+}$, $C^{6+}$, $O^{8+}$ |
| Beam pulse length: | ≤200 μs, ≤5 Hz |
| Beam emittance (normalised): | (0.6 μ mm mrad |
| Momentum spread (incl. stripping foil): | $\pm 1.5 \times 10^{-3}$ |

Synchrotron - main parameters
Injection:

| | |
|---|---|
| Multiturn injection, number of turns: | 15 |
| Injection energy: | 7 MeV/u |
| Magnetic rigidity of injected beams: | 0.38–0.76 Tm. |
| Acceptance: horizontal: | 100 π mm mrad |
| vertical: | 25 π mm mrad |

Ring parameters:

| | |
|---|---|
| Circumference: | 63.246 m |
| Superperiodicity: | 2 |
| Lattice: | DOUBLET |
| Tune: horizontal $Q_h$: | 1.674 |
| vertical $Q_v$: | 1.221 |
| Bending magnets: number: | 6 |
| deflection angle: | 60° |
| radius of curvature: | 4.4 m |
| maximum flux density: | 1.50 T |
| aperture: | $A_{horizontal}$ = 180 mm, $A_{vertical}$ = 70 mm |
| Quadrupoles: number: | 12 |
| effective length $L_{eff}$: | 0.5 m |
| maximum gradient: | 5.5 T/m |
| number of families: | 2 focusing and 1 defocusing |
| Sextupoles: number: | 4 |
| maximum strength: | 7 T/m² |
| effective length $L_{eff}$: | 0.2 m |
| number of families: | 2 |

Parameters of the extracted beams:

| | |
|---|---|
| Beam energy: | 50–430 MeV/u |
| Magnetic rigidity: | 1.03–6.60 Tm |
| Emittance: horizontal (max.): | 5 π mm mrad |
| vertical (max.): | 5 π mm mrad |
| Momentum spread: | ±0.1% |

TABLE 2

The output beam parameters of the designed carbon injector chain

| | |
|---|---|
| Ion species to the synchrotron (after stripping) | protons, $^4He^{2+}$, $^{12}C^{6+}$, $^{16}O^{8+}$, $^3He^{1+}$ |
| Beam energy | 7 MeV/u |
| Pulse current after stripper | ≈100 eμA ($C^{6+}$) |
| Beam pulse (linac output) | ≤200 μs, ≤5 Hz |
| Beam pulse after chopper | 30 μs |
| Duty cycle | ≈0.1% |
| Normalized beam emittance | ≤0.6π mm mrad |
| Momentum spread (including stripper) | $\pm 1.5 \times 10^{-3}$ |
| Total projected length up to the stripper | ≈13.5 m (including ion source) |

TABLE 3

List of components of the synchrotron ring Ion Cancer Therapy

| Component | Number | assignment in FIG. 4 |
|---|---|---|
| Main dipole magnet | 6 | BM—bending magnet |
| Quadrupole magnet | 12 | QF—focusing quadrupole |
| | | QD—defocusing quadrupole |
| Sextupole | 4 | Sxc—sextupole for chromaticity correction |
| | | Sxr—sextupole for separatrix production |
| Extraction septum magnet | 2 | SM—septum magnet |
| Bumper magnet | 3 | BMP—bumper magnet |
| RF-Cavity | 1 | RF—radiofrequency cavity |
| Electrostatic injection septum | 1 | Esinj—electrostatic septum-injection |
| Electrostatic extraction septum | 1 | ESextr—electrostatic septum-extraction |
| Horizontal RF-exciter | 1 | Rfex—RF exciter |
| Vertical steerer | 6 | |
| Horizontal steerer (auxilliary windings) | 6 | |
| Position pick-up | 6 | |
| Beam transformer (fast/slow) | 2 | |

TABLE 4

The main parameters of the gantry Gantries

| | |
|---|---|
| Number: | 2 |
| Arrangement: | single plane, 'barrel'-like isocentric gantry, the scanning system located upstream the last bend-down dipole magnet |
| Scanning system: | two-direction magnetic scanning, parallel mode of scanning (SAD ≈ 50 m) |
| Angle of rotation: | 360° |
| Ion-optical functions: | zero-to-zero dispersion matching, beam-size control at the isocentre |
| Overall dimensions: | Radius (including the magnet yoke): 540 cm<br>Length: 1756 cm<br>Weight: ≈160 tons<br>Drift to the patient: 140 cm<br>Scanning area: 20 × 20 cm² |
| Main components: | 2 × 42° dipole magnets,<br>1 × 90° dipole magnet,<br>8 quadrupole magnets, one horizontal scanner,<br>one vertical scanner,<br>beam-monitoring block |
| Last dipole magnet: | normalconducting, $B_{max}$ = 2 T, 37 tons, 580 kW |
| Quadrupoles: | $L_{eff}$ = 30 cm<br>Aperture radius = 30 mm<br>Field gradient (max.): 25 T/m |
| Acceptance (max.): | |
| horizontal: | 5π mm mrad |
| vertical: | 5π mm mrad |
| Parameters of the transported beams: | Energy: 50–430 MeV/u<br>Magnetic rigidity: 1.03–6.6 Tm<br>Momentum spread: 0.2% |

TABLE 5

Parameters of the scanning magnets

| | The horizontal scanner | The vertical scanner |
|---|---|---|
| Maximum flux density | 0.38 T | 0.38 T |
| Ramping rate | 38 T/s | 10 T/s |
| Maximum bending angle | 1.45° | 3.3° |
| Magnetic length | 0.546 m | 1.220 m |
| Lamination thickness | 0.3 mm | 0.3 mm |
| Construction length | 0.6 m | 1.3 m |
| Aperture | 140 mm × 130 mm | 170 mm × 170 mm |
| Maximum current | 400 A | 400 A |
| Conductor cross-section | 8.5 mm × 8.5 mm | 8.5 mm × 8.5 mm |
| Number of turns | 96 | 128 |
| Power consumption | 11 kW | 25 kW |
| Weight | 275 kg | 725 kg |

What is claimed is:

1. An ion beam therapy system comprising:
   a source of ions (300);
   an accelerator system (400) for accelerating ions as a beam (50);
   an ion beam transport system (60) for directing an ion beam from the accelerator to treatment stations (100) to treat patients supported in fixed orientation by patient support (200),
   wherein said ion beam transport system (60) comprises: at least a horizontal beam delivery system and at least a gantry (8) rotatable about an axis of rotation,
   said gantry carries optics for receiving the ion beam on its axis of rotation (80), transporting said ion beam away from the axis of rotation and returning the ion beam on a path intersecting the axis at a target isocentre (90) within the patient, delivering said ion beam (50) by rotation of the gantry to said target isocentre (90) from different angles between 0 and 360 degrees;
   said gantry (8) and said horizontal beam delivery system carries means (45, 55) for raster scanning said ion beam (50), enclosing vertical deflection means (45) and horizontal deflection means (55), positioned upstream of a last bending magnet (65), directing said ion beam (50) towards the patient and downstream the last quadrupole lens (75) of said gantry (8),
   characterized in that the system comprises
   the plurality of separate patient treatment stations (100) each having the patient support (200) for orienting a patient in a fixed position; and
   wherein said vertical deflection means (45) and said horizontal deflection means (55) for said raster scanning each comprises one scanning magnet and deflects said ion beam (50) perpendicular to its beam axis, so that the beam (50) can be scanned by two scanning magnets over a predetermined controlled area around said target isocentre (90) after passing said last bending magnet (65), which provides a parallel scanning mode by an edge focusing effect at its entrance and exit edges and which comprises a normal conducting last dipole magnet.

2. The ion beam therapy system according to claim 1, characterized in that the ions of said ion beam (50) are one out of the group helium, carbon or oxygen ions.

3. The ion beam therapy system according to claim 1, characterized in that the system further comprises a position emission tomography camera oriented towards an inbeam position.

4. The ion beam therapy system according to claim 1, characterized in that the accelerator system (400) comprises a linear accelerator (22) and a Synchrotron (23) accelerator.

5. The ion beam therapy system according to claim 4, wherein the rigidity of an injected ion beam injected into said Synchrotron (23) accelerator is in the range of 0.38 to 0.76 Tm.

6. The ion beam therapy system according to claim 1, characterized in that said system comprises means for monitoring the raster scanned beam after passing the last bending magnet (65).

7. The ion beam therapy system according to claim 6, characterized in that said means for monitoring are mounted in-beam to a common support upstream of the patient support (200) and downstream the last bending magnet (65) coupled to the gantry (8) or upstream of the patient on a movable support for said monitoring means.

8. The ion beam therapy system according to claim 6, characterized in that said monitoring means comprise parallel-plate-ionisation chambers and multi-wire proportional chambers.

9. The ion beam therapy system according to claim 1, characterized in that the last bending magnet (65) has a bending angle of more than 60°.

10. The ion beam therapy system according to claim 1, wherein an extraction mode of the extraction procedure is providing a variable extraction time between 1 and 10 seconds adapted to a tumor painting time for completion of a tumor slice and a beam monitoring time.

11. The ion beam therapy system according to claim 1, wherein values of emittances of extracted beams depend upon beam properties at injection includes the extraction beam energy, the extraction procedure and the Synchrotron (23) settings before the extraction starts.

12. The ion beam therapy system according to claim 1, wherein an extraction system (SM) provides a switching off and on within the same Synchrotron (23) cycle having the same beam energy.

13. The ion beam therapy system according to claim 1, wherein the optical properties at the gantry (8) are an achromatic beam transport from the Synchrotron (23) to a coupling point of the gantry (8), beam waists in both planes and an equal beam size in horizontal and vertical planes.

14. The ion beam therapy system according to claim 1, wherein an energy beam transport system (60) comprises quadrupole lenses (Q, 75), bending magnets (BM, 65) and beam diagnostic devices.

15. The ion beam therapy system according to claim 1, wherein an abort chopper for emergency switch off is installed subsequent to an extraction magnet.

16. An ion beam therapy system comprising:
a source of ions (300);
an accelerator system (400) for accelerating ions as a beam (50);
an ion beam transport system (60) for directing an ion beam from the accelerator to the treatment stations (100) to treat patients supported in fixed orientation by the patient support (200),
wherein said ion beam transport system (60) comprises: at least a horizontal beam delivery system and at least a gantry (8) rotatable about an axis of rotation, a plurality of separate patient treatment stations (100) each having a patient support (200) for orienting a patient in a fixed position;
characterized in that
the therapy system provides a multifield intensity-controlled raster scan treatment facility, comprising:
a Synchrotron (23) accelerator chain providing a pulse-to-pulse variation of beam energy and intensity in parameter intervals of 50–430 MeV/n for the extraction beam energy and of 1:1000 ratio between a minimum and a maximum beam intensity,
an extraction system (SM) providing a variation of the spill-duration and a switching off and on the extraction process within the same Synchrotron (23) cycle having the same beam energy at the same flat-top level
an injection chain providing a switching between different ion species within less that 30 minutes,
a control and safety system having an abort chopper emergency switch off, installed subsequent to an extraction magnet, avoiding a patient irradiation in case of components failures or incorrect beam properties
a gantry beam delivery system (8) providing a $4\pi$ tumor targeting equipped with an intensity controlled raster scanning system having two scanning magnets (45, 55) upstream of a last bending magnet (65), which provides a parallel scanning mode by an edge focusing effect at its entrance and exit edges and which comprises a normal conducting last dipole magnet.

17. The ion beam therapy system according to claim 16, wherein the rigidity of an injected ion beam injected into said Synchrotron (23) accelerator chain is in the range of 0.38 to 0.76 Tm.

18. The ion beam therapy system according to claim 17, wherein an extraction mode of the extraction procedure is providing a variable extraction time between 1 and 10 seconds adapted to a tumor painting time for completion of a tumor slice and a beam monitoring time.

19. The ion beam therapy system according to claim 18, wherein values of emittances of extracted beams depend upon beam properties at injection the extraction beam energy, the extraction procedure and the Synchrotron (23) settings before the extraction starts.

20. The ion beam therapy system according to claim 16, wherein the optical properties at the gantry (8) are an achromatic beam transport from the Synchrotron (23) to a coupling point of the gantry (8), beam waists in both planes and an equal beam size in horizontal and vertical planes.

21. The ion beam therapy system according to claim 16, wherein an energy beam transport system (60) comprises quadrupole lenses (Q, 75), bending magnets (BM, 65) and beam diagnostic devices.

22. A method for operating the system according to claim 1 comprising the steps of:
generating selected ions selected out of the group Helium, carbon or oxygen ions of a specific isotope;
forming an ion beam of said ions and selecting said isotope by mass spectrometric means;
accelerating said ion beam by linear accelerating means (22) and Synchrotron (23) means;
transferring said ion beam (50) along to said axis of rotation of a rotatable gantry (8);
bending said ion beam away from said axis around the perifering of said gantry (8);
characterized by
scanning said ion beam by deflecting said ion beam (50) in a vertical and horizontal direction in respect to the axis of said ion beam before said ion beam is bent by a last bending magnet (65) which provides a parallel scanning mode by an edge focusing effect towards the isocentre of said gantry (8).

23. The method for operating the system according to claim 22, wherein the rigidity of the injected ion beam injected into said Synchrotron (23) accelerator chain is maintained in the range of 0.38 to 0.76 Tm.

24. The method for operating the system according to claim 22, wherein the extraction mode of the extraction process provides a variable extraction time between 1 and 10 seconds adapted to a tumor painting time for completion of a tumor slice and a beam monitoring time.

25. The method for operating the system according to claim 22, wherein the values of emittances of the extracted beams depend upon beam properties at injection, extraction beam energy, the extraction process and the Synchrotron (23) settings before the extraction starts.

26. The method for operating the system according to claim 22, wherein the extraction process provides a switching off and on within the same Synchrotron (23) cycle having the same beam energy.

27. The method for operating the system according to claim 22, wherein a pulse-to-pulse variation of beam energy and intensity is performed by an accelerator chain (23) in parameter intervals, of 50–430 MeV/n for extraction beam energy and of 1:1000 ratio between a minimum and a maximum bean intensity.

28. The method for operating the system according to claim 22, wherein a variation of the spill-duration and a switching off and on the extraction process at the same flat-top level is performed by an extraction system.

29. The method for operating the system according to claim 22, wherein a switching between different ion species is performed by an injection chain within less than 30 minutes.

30. The method for operating the system according to claim 22, wherein in the case of components failures or incorrect beam properties a control and safety system avoids a patient irradiation.

* * * * *